(12) United States Patent
Kirchheim et al.

(10) Patent No.: US 8,113,035 B2
(45) Date of Patent: Feb. 14, 2012

(54) METHOD FOR THE DETECTION OF GASEOUS IMPURITIES IN MATERIALS

(76) Inventors: Reiner Kirchheim, Gottingen (DE); Peter-Joachim Wilbrandt, Gottingen (DE); Jurgen Gegner, Forth (DE)

( * ) Notice: Subject to any disclaimer, the term of this patent is extended or adjusted under 35 U.S.C. 154(b) by 549 days.

(21) Appl. No.: 12/298,317

(22) PCT Filed: Apr. 25, 2007

(86) PCT No.: PCT/EP2007/003619
§ 371 (c)(1),
(2), (4) Date: Oct. 24, 2008

(87) PCT Pub. No.: WO2007/121994
PCT Pub. Date: Nov. 1, 2007

(65) Prior Publication Data
US 2009/0241639 A1    Oct. 1, 2009

(30) Foreign Application Priority Data
Apr. 25, 2006  (DE) .................. 10 2006 020 426

(51) Int. Cl.
*G01N 33/20* (2006.01)
*G01N 7/00* (2006.01)
(52) U.S. Cl. .................. 73/31.03; 73/19.07; 436/144
(58) Field of Classification Search ............. 73/19.07, 73/31.03; 436/144
See application file for complete search history.

(56) References Cited

U.S. PATENT DOCUMENTS

| 2,731,403 A | * | 1/1956 | Rubin | 205/138 |
| 2,785,285 A | * | 3/1957 | Bernard | 219/146.22 |
| 2,926,981 A | * | 3/1960 | Stout et al. | 445/55 |
| 3,452,585 A | * | 7/1969 | Vilinskas | 73/19.07 |
| 3,732,076 A | * | 5/1973 | Toy et al. | 436/144 |
| 3,909,617 A | * | 9/1975 | Jones et al. | 250/493.1 |
| 4,043,387 A | * | 8/1977 | Lamp | 165/104.27 |
| 4,192,175 A | * | 3/1980 | Godai et al. | 73/19.02 |
| 4,555,275 A | * | 11/1985 | Tobin | 148/277 |
| 7,306,951 B1 | * | 12/2007 | Benson et al. | 436/144 |

FOREIGN PATENT DOCUMENTS

| EP | 0015428 A1 | * | 9/1980 |
| JP | 60-94467 | * | 5/1985 |
| JP | 61-133278 | * | 6/1986 |
| JP | 62-39671 | * | 2/1987 |
| JP | 1-110573 | * | 4/1989 |
| JP | 1-319575 | * | 12/1989 |
| JP | 4-123866 | * | 4/1992 |

OTHER PUBLICATIONS

Cardarelli, F. et al., "Tantalum Protective Thin Coating Techniques for the Chemical Process Industry: Molten Salts Electrocoating as a New Alternative", International Journal of Refractory Metals and Hard Materials, vol. 14, (1996), pp. 365-381.*

* cited by examiner

*Primary Examiner* — Daniel Larkin
(74) *Attorney, Agent, or Firm* — Kevin L. Bray

(57) ABSTRACT

Disclosed is a method for detecting hydrogen in steel. According to the method, hydrogen contained in steel is transferred into and preferably concentrated in at least one second material. Representative second materials include metals such as vanadium, niobium, tantalum, and their alloys. Upon transfer to the second material, the hydrogen is detected and preferably quantitatively determined. The data obtained with the method enables conclusions to be drawn about the presence of hydrogen in steel. Preferably, the concentration of hydrogen in steel is quantitatively determined from information obtained about the presence of hydrogen in the second material.

27 Claims, No Drawings

METHOD FOR THE DETECTION OF GASEOUS IMPURITIES IN MATERIALS

CROSS-REFERENCE TO RELATED APPLICATIONS

This application claims priority from German Application No. 102006020426.3, filed Apr. 25, 2006, and from International Application Serial No. PCT/EP2007/03619 filed Apr. 25, 2007.

FIELD OF INVENTION

The invention is mainly a method for detecting impurities, especially gasses, in a first material, especially in metallic materials.

BACKGROUND OF THE INVENTION

It is a known fact that certain unwanted amounts of foreign components in other materials, namely metallic materials, have negative consequences on the physical and chemical properties of these materials. Thus it is undesirable, that a metal or a metallic alloy contains certain amounts of other metals. An example is the unacceptable lead content in a copper alloy, which are used for water-bearing components in sanitary facilities.

The complex problem mentioned above is important notably for gaseous impurities, because the corresponding atoms are in different materials, namely metallic materials, soluble in comparably high concentrations and on the other hand in many cases highly mobile in these materials. Such gaseous impurities often affect materials properties in an undesirable way.

Among the gaseous impurities special emphasis has to be placed on hydrogen. Its severe negative effect on materials, especially metallic materials, is known for some time by the term hydrogen embrittlement. Especially in steels, and parts or work pieces made out of steel, a considerable impairment of performance has to be expected.

Especially for steels the unwanted absorption of hydrogen occurs during its production, as well as during its finishing and during its application. As examples the processes of casting, welding, bating and galvanizing are mentioned (Hoffmann, F.: Linkewitz, T.; Mayr P.: Wasserstoffversprödung—Meinungen und Fakten. In: Einsatzhärtung. Berichtsband der AWT-ATTT-Tagung, 29.-30. April 1998, Aachen, Arbeitsgemeinschaft Wärmebehandlung und Werkstofftechnik e.V. (AWT)/Association) Technique de Traitment Thermique (ATTT), Wiebaden (1998) S. 259-267; Hoffmann, F.: Linkewitz, T.; Mayr P.: Wasserstoffaufnahme beim Einsatzhärten. HTM 54 (1999) 10-12).

In addition, the incorporation of hydrogen in heat treated steel components, namely from the gas phase during carbonization, is especially high (Wyss, U.: Aufkohlen in Gasen. In: Benninghoff, H. (Hrsg.); Wärmebehandlung der Bau-und Werkzeugstähle. BAZ Verlag, Basel/1978). By this process hydrogen is generated during the primary decomposition reaction of carbonizing reactants forming the gaseous atmosphere and via surface reactions leading to the formation of carbon. Also, during the so-called direct hardening, a concentration of 2.2 weight ppm (ppm by weight) hydrogen (which corresponds to 122.1 atomic ppm) can be attained. (Streng, H.; Grosch, J.; Razim, C.: Wasserstoffaufnahme und-abgabe beim Einsatzhärten. HTM (Härterei-Technische Mitteilungen) 42 (1987) 245-260). Because of the high mobility of hydrogen atoms within the iron lattice of the steel hydrogen is distributed over the entire volume of the material during usual carbonizing times. Therefore, the typical "fish eyes" at inclusions occur also within internal regions of thick components.

In addition, hydrogen may also form and enter materials during corrosion of metallic alloys in hydrogen containing media. Thus hydrogen is entering from the surface into the steel component during the service of lubricated engine parts via tribochemical reactions.

The features of hydrogen embrittlement and the preceding events in the material are studied and discussed for a long time. An attempt was made to explain the damage caused by hydrogen with for principal mechanisms (Neumann, P.; Grundlagen der Wirkung von Waserstoff auf die Rissbildung in Stälen. Stahl and Eisen 107 (1987) 577-583). These four mechanisms are:

Formation of crack tips at brittle carbides due to the three axial stress state.

Internal formation of methane by hydrogen reacting with dissolved carbon (internal decarburization).

Direct mechanical damage by high hydrogen equilibrium pressures (recombination of the dissolved hydrogen atoms to hydrogen molecules, especially at defects).

Decrease of the cohesion forces by hydrogen accompanied by a disposition to brittle fracture.

For gaseous impurities, especially for the described hydrogen embrittlement, it is not only problematic that embrittlement occurs but also that the effect of these gaseous impurities cannot be detected with sufficient sensitivity. Basically it is possible in the case of hydrogen to detect it quantitatively. Though for quantitative determinations, which are indispensable for a fundamental understanding of the underlying processes, no sufficiently sensitive techniques are available, or the available techniques are not or not sufficiently applicable in the environment of the fabrication or operation of the corresponding materials.

Especially a quantitative determination is also for the state of the art known U.S. Pat. No. 3,732,076 not conceivable. There the determination of hydrogen is conducted via microscopic or electron microscopic observation. Based on the resulting inaccurate data of the used samples a reproducible quantitative determination of hydrogen concentrations is not possible.

In this context it is known from the publication of R. Kirchheim, Acta Metallurgica, Vol. 27, Issue 5, pp. 869 to 878 (1979), that the diffusion coefficient of oxygen in copper, niobium and tantalum can be determined with the aid of metals in which oxygen has a higher solubility. In this nearly 30 years old publication neither the set of problems associated with gaseous impurities nor their detection is mentioned. The issue of hydrogen embrittlement is not addressed as well.

Accordingly the present invention concerns the detection of high sensitivity impurities, namely gaseous impurities, in materials, especially in metallic materials. Thereby a quantitative determination of these impurities may become possible. On the other hand the present invention also has the goal to provide a method by which materials, especially metallic materials, are protected against gaseous impurities or their concentration is reduced. Namely the negative effect of hydrogen shall be diminished or eliminated.

SUMMARY OF THE INVENTION

On the one hand the invention comprises a method of the kind mentioned before, in which the impurities contained in the first material are at least partly transferred into a second material. This step of the method occurs preferentially by enriching the impurities in the second material.

Further on the presence of the impurities will be detected in the second material by the method of this invention, whereby preferably the concentration in the second material will be determined quantitatively.

Furthermore the presence of the impurities in the first material will be deduced by the method of this invention, whereby here as well the concentration in the first material will be determined quantitatively preferably.

The outlined method of the invention may be described as well by a transfer of impurities from the first material into a second material, in which the impurities are detected easier or better. The actual (direct) detection of the impurities will be conducted in the second material, and from this detection in the second material conclusions are drawn about the presence of the impurities in the first material. Considering the first and second material as an entity the invention leads to a transfer/enrichment of the impurity in well-defined regions of the entity, by which conclusions become possible about the remaining regions of the entity.

As mentioned before, the impurities or unwanted components in the first material are mainly meant to be gaseous impurities. The expression "gaseous impurities" shall mean that the corresponding atoms or molecules of the impurity exist in their "normal" aggregate state as gases. Thereby it shall be understood that the gaseous impurities, especially in the case of the gaseous impurities, could be present in the materials in different form. For instance the gaseous elements hydrogen $H_2$, oxygen $O_2$ and nitrogen $N_2$ and others are as a rule and namely at low concentrations dissolved atomically in the corresponding materials, where they occupy interstitial lattice sites or sites near lattice defects. At higher concentrations the dissolved atoms recombine to the corresponding molecules, namely at defects.

The impurity in the method of the invention is preferentially hydrogen. As mentioned before in the context of material damage and describing the state of the art, the negative effect of hydrogen on materials properties is especially important.

The first material, in which the presence of impurities has to be determined, finally, shall be as mentioned before preferentially a metallic material. The method of this invention is especially applied to steels. Here the invention is in an exceptional way suitable for those cases where hydrogen as an impurity has to be detected in steel.

As a second material in the invention any material may be used in principal, in which the detection of the corresponding impurity can be conducted easier or better relative to the first material. For gaseous impurities the second material is as a rule a material, in which the corresponding gaseous impurity has a higher solubility and/or a higher diffusivity when compared with the examined first material. In the case of hydrogen as an impurity, the second material is presumably a noble metal like palladium and its alloys. Furthermore vanadium, niobium or tantalum and their alloys are considered preferable.

The transfer/enrichment of the impurities from/of the first material in the second material shall be described in more detail in the following (in a non-restrictive way) for the case of hydrogen as an impurity.

From the foregoing description it follows that the second material acts as a sink for the impurity hydrogen because of its larger thermodynamic affinity to hydrogen. One may also say that the second material acts like a vacuum cleaner or an absorber sucking hydrogen out of the first material. For the gaseous impurity of hydrogen the corresponding transfer from the first into the second material occurs in a relative short time. This may be exemplified for hydrogen by estimation as follows:

The first material shall be a sample of 200 µm thickness onto which a 20 nm thick surface layer of the second material is deposited. In the specimen of the first material the hydrogen concentration may be 1 weight ppm. This is the typical order of magnitude for technical steels corresponding to 55.5 atomic ppm. If the total amount of hydrogen will be transferred into the layer of the second material, its concentration will be raised to 55.5 at.-% hydrogen (assuming the same lattice constant). For a typical diffusion coefficient for hydrogen in ferritic iron alloys of $D=1E-6$ cm$^2$/s the enrichment in the second material by unhindered diffusion occurs within a time of about 100 seconds.

This plausibility consideration shows for hydrogen not only that the transfer from the first into the second material happens in a relative short time but also that for a known thickness of the layer of the second material and the known hydrogen diffusion coefficient in the specimen of the first material a direct evaluation of the hydrogen concentration in the first material becomes achievable by a quantitative determination of the hydrogen content in the second material. There is a direct relation between the hydrogen concentration in the layer of the second material and the hydrogen concentration in the underlying microstructural regions of the specimen of the first material.

This will be explained in more detail in the following in connection with the given example.

As mentioned before, by the method of this invention the transfer of the impurity from the first into the second material occurs mainly by diffusion. This diffusion will be for certain impurities, e.g. hydrogen, already sufficient at room temperature. For other impurities it may be advantageous, if the transfer/enrichment of the impurity in the second material is conducted at higher temperatures, in order to achieve higher diffusivities and/or higher solubilities.

The transfer of the impurity from the first into the second material can be particularly realized in this invention by applying an electric field (if needed, by applying a magnetic field also alternatively or additionally). By these means the diffusion of the impurities from the first material into the second one can be initiated or supported.

To guarantee an unhindered transfer/enrichment of the impurity form the first into the second material, the contact between first and second material has to be sufficient. It may already be sufficient to get this contact, preferably a perfect contact, at single regions. Preferentially the contact, especially the perfect contact, between the two materials is realized over the whole surface regions. This way the impurity is transferred as quick and as complete as possible from the first into the second material.

As a rule of this invention the second material can be chosen such that it has a much higher affinity for the impurity than the first material. This way small volumes of the second material when compared with the volume of the first material can be used and can be sufficient. This has the additional advantage that in smaller volumes of the second material larger concentrations of the impurity (and, therefore, larger enrichments of the impurity) are reached. This facilitates the detection of the impurity in the second material, especially its quantitative determination.

In agreement with the last statements it is therefore in this invention preferred, if the second material is deposited as a layer, especially as a thin layer onto the substrate or specimen of the first material. Thereby the layer is placed at least partly on the surface of the substrate or specimen, preferentially on the whole surface of the substrate or specimen.

The dimensions, e.g. the thickness of the substrate or specimen are principally not crucial in this invention. As deduced before, the diffusion occurs, namely for the case of hydrogen as an impurity, even for thicker samples in sufficiently short times. For these cases other geometries than a thin layer of the second material are conceivable. Thus for instance the second material can be contacted to the first material in longish or elongated form, respectively, namely as a band, bolt, wire or such, for example a vanadium wire is brought into contact with the first material for instance by welding, especially friction welding and for example the amount of hydrogen absorbed by vanadium can easily be monitored via the changing electrical resistivity.

Friction welding is known as a method of welding during which two parts are moved relative to each other and the two parts touch each other at the area of contact. Through friction, heat is generated. At the end of the event of friction, the parts are positioned and joined to each other under pressure, under high pressure as a rule. The advantage of friction welding lies in the fact that a distinctly smaller region of the corresponding parts will be heated up in comparison with other methods of welding and that as a rule no melting occurs in the zone where both parts are joined.

For the case of a layer-geometry the layer thickness of the second material is preferably less than 1 μm, preferably less than 250 nm. In addition, layer thicknesses of the second material between 10 and 100 nm are preferred. Especially layer thicknesses of the second material of ca. 20 nm can be chosen. For the usual dimensions of the corresponding substrates/specimens the enrichment of the impurities in the layer achieved this way will be sufficient.

The differently shaped second material, especially the described layers of the second material, can principally be deposited onto the corresponding substrates or specimens of the first material by the most different methods. Preferentially mentioned here are the so-called CVD (chemical vapour deposition) techniques and especially the PVD (physical vapour deposition) techniques. CVD-techniques use the chemical deposition of layers out of the gas phase. Thereby a solid component as formed by a chemical reaction from the gas phase is deposited onto a heated surface of a substrate. PVD-techniques are a group of film deposition methods, by which the layer is formed during condensation of the vapour of a material. Often an ion beam or a laser beam is directed onto a so-called target of the material being deposited and thereby atomizing this material. This atomized material is then deposited onto the surface of the substrate.

If the second material shall be connected to the first material as a thick layer, an immediate and intimate contact can be achieved by plastic deformation of the regions of contact (i.e. by friction welding, explosive plating or powder spraying) or by thermal welding. For the case of hydrogen the total or partial removal of the possible natural and dense oxide layers of the first and second material is appropriate or required, because these oxide layers can interrupt or at least strongly suppress the hydrogen transfer between the materials.

For the method of this invention the presence of the impurity in the second material can also be detected or, if necessary, be determined quantitatively by the most different techniques. Here wet chemical detection methods or thermodesorption (TDS) are possible. A preferred detection for instance is done by X-ray diffraction (XRD), by which the enrichment of hydrogen in the corresponding material is deduced from the change of the lattice constant of this material. Thus for instance an increase of the hydrogen concentration from 0 to 1 at.-% leads in the material niobium to a relative change of the lattice constant of $5 \times 10E-4$. Such changes of the lattice constant can be measured with modern X-ray diffractometers. The terminal solubility of hydrogen in niobium is about 6 at.-% at 295 K and at higher concentrations a second phase with its characteristic Bragg peaks is formed. From the ratio of the intensities of the hydride phase and the $\alpha$-phase the volume fractions of these phases can be calculated and, therefore, the total hydrogen content absorbed by the niobium is obtained.

A likewise especially preferred method of detection is the measurement of the electrical resistivity, which is especially useful for those cases, where the second material is applied as wires, bolts or ribbons. In this case an increase of the hydrogen concentration of 0.1 at.-% in vanadium causes an increase of the specific resistivity of 0.01 μOhm cm. This and even smaller changes can be measured directly or even more sensitive as a difference measurement to a vanadium sample of the same geometry but not being in contact with the first material.

An additional preferred technique of this invention for detecting the impurity, especially hydrogen, in the second material is an electrochemical one, in which the first and second materials are parts of a galvanic cell. The sample of the first material and the connected layer of the second material form the working electrode of the galvanic cell and will be arranged with a reference and counter electrode in such a way that an appropriate potential is applied leading to an electrochemical hydrogen depletion.

The exact analysis of the data which are obtained during the transfer/enrichment of the impurity in the second material will be explained in more detail in the context of an example. At this point it will be mentioned in advance only that it will be preferred in this invention to calculate the amount of the impurity absorbed by the second material (at the contact area between the first and second material) as a function of time and divided by the contact area. This normalized amount of the impurity will be used as a quantity for the property of the first material affected by the impurity. For the case of hydrogen as an impurity this quantity serves as a quantity for the tendency of the first material to become embrittled by hydrogen.

The explanations given within the example demonstrate also that the method of the invention allows statements about the binding strength of the impurity, especially hydrogen, within the first material. In this context it is intended for preferred realisations of the method of this invention to transfer the impurity, namely hydrogen, in at least two, preferentially more than two second materials and to derive the binding strength of the impurity within the first material. Depending on the affinity of the second material to hydrogen the fraction of differently bound atoms or molecules of the impurity, especially hydrogen, in the first material can be determined. This will also be explained in more detail in the context of the example.

Besides the previously described method for detecting hydrogen the invention covers also a method for protecting the first material, especially metallic materials, against impurities, especially gaseous impurities. This method is characterized by contacting the first material with at least one second material, which has a higher thermodynamic affinity to the impurity when compared to the first material. Thus the impurity will be at least partly transferred from the first into the second material, preferentially leading to an enrichment of the impurity in the second material.

For this method the impurity is preferably hydrogen, too and the metallic material is preferentially steel. As a second material, preferably vanadium, niobium and tantalum can be used as well. In this case as well the second material is preferentially applied as a layer connected with at least a part of the surface of the substrate or specimen of the first material.

With respect to the method of protecting a first material it will be explicitly referred to the explanations given before regarding the detection techniques.

Finally the invention comprises a method for reducing the concentration of impurities, especially gaseous impurities, in a first material, especially in metallic materials. This method is wherein said first material is contacted with at least one second material, which has a higher thermodynamic affinity to the impurity in comparison with the first material causing the at least partial transfer of the impurity from the first into the second material. Thereby the impurity will preferentially be enriched in the second material.

With respect to this additional method, too it will be explicitly referred to the extensively described techniques for detecting the impurities given before.

All explanations regarding the method of detection described before shall hereby become a part of the explanation of the method protecting a first material and of the method of reducing the concentration of impurities.

The advantage of the last two described methods lies in the fact that a substrate or a specimen of the first material can be effectively protected against an impurity, especially a gaseous impurity like hydrogen, or that this impurity within this material can be depleted effectively.

Thus for instance it is possible, on parts of the surface of a work piece or on the whole surface of a work piece, which for instance will be made out of steel (bearing, cam shaft, gear wheels) to deposit a layer of a (second) material, which absorbs the impurity, especially hydrogen. The described incorporation/attachment of ribbons, bolts or wires of the second material is preferred as well. Then the impurity, especially hydrogen, will be continuously transferred during normal service of the work piece from the base material (first material) into the second material and if necessary enriched there. Accordingly the impurity remains in the base material below a critical concentration and will do no harm anymore.

If the layer or any other shaped structure of the second material will be saturated with the impurity such that it does not absorb impurities any further, the layer of the second material can be removed and a new layer of the second material can be deposited. For preferred methods of application it is possible, too, "to deplete" the original layer, that means to remove for instance hydrogen from the layer. This can be achieved for instance by an electrochemical technique.

For the invention it is possible in these cases, too, to test by the described techniques selectively on-site how high the concentration of the impurities is in both the layer of the second material as well as in the base material. This way the bothersome concentrations of an impurity can be checked.

As a consequence of the explanations given before the invention also covers the application of the second material as a probe for detecting impurities in the first material. In agreement with the previous explanations the second material could be vanadium, niobium or tantalum. The impurity is a gaseous impurity, especially hydrogen. The first material, in which the impurity shall be detected, is especially steel.

Finally the invention covers an object (article) of the first material, especially steel, whereby the object preferentially is a substrate or a specimen of this first material. In the sense of the invention this object was contacted with at least one second material for detecting impurities, for protecting from impurities and/or for reducing the concentration of impurities. Regarding the last explanations the second material is preferentially composed of vanadium, niobium or tantalum. With these objects and materials especially gaseous impurities, preferably hydrogen shall be detected.

For preferred cases of application of the objects regarding the invention the second material is contacted in a longish shape, especially as a ribbon, bolt, wire or similar to the object of the first material. The way of contacting can be for instance welding, especially friction welding. Hereby it will be explicitly referred to and recommit to the previous explanations in the description.

For other preferred cases of application of the objects regarding the invention the second material is deposited as a layer, preferentially as a thin layer. Here as well it will be explicitly referred to and recommit to the previous explanations in the description.

Additional features of the invention are deduced from the following description of a preferred case of application in connection with the dependent claims. Hereby the particular features can be realized as a single one or as a combination of many of them. The described example serves solely as an explanation and for a better understanding of the invention and is by no means to be identified as restricting the invention.

EXAMPLE 1

From a thin sheet (thickness d=1 mm) of a construction steel, which has a hydrogen concentration as determined by the hot extraction technique of about (0.5±0.1) wt.-ppm, the natural oxide layer was removed by sputtering under ultra high vacuum conditions and a niobium layer is deposited with a thickness of about 200 nm by a PVD-method. The molar volume of the niobium layer $V_a$ ($_a$ means absorbing) is 10.8 cm$^3$/mole. The niobium layer was covered with a 5 nm thick Pd-layer. Thus the niobium layer is protected from oxidation and an electrochemical determination of hydrogen becomes possible.

The initial concentration of hydrogen in steel $c_0$ of 0.5 wt.-ppm corresponds to 3.9E−6 mole−H/cm$^3$. The diffusion coefficient of hydrogen in the used steel D will be assumed to be D=1E−6 cm$^2$/s. The almost complete absorption of hydrogen into the niobium layer is attained within a time of ca. d$^2$/D=1E4 s.

After a waiting time of four hours the X-ray diffraction peaks of the solid solution phase of niobium with a hydrogen content of H/Nb=0.06 and the peak of the niobium hydride with H/Nb=1 will be measured. From the fraction of the areas below the X-ray peaks the total hydrogen content within the niobium layer will be calculated to be mole-H/mole-Nb=0.20 or 1.8E-2.

The calculation for the conducted experiment can be described as follows:

In the present case it will be assumed that the whole hydrogen amount contained within the steel is transferred into the niobium layer and will be enriched there. As mentioned before, the volumes of the studied specimen $V_P$ (here a technical steel as the first material) and of the absorber $V_A$ (here niobium as a second material) will be advantageously dimensioned in this invention such that the absorption capacity of the absorber will not be exceeded.

Accordingly the amount of hydrogen, which will be supplied by the specimen, is equal to the amount of hydrogen, which will be included in the absorber. The hydrogen concentration in the specimen is calculated from the measured hydrogen concentration in the absorber by:

$$C_A = \frac{V_P}{V_A} C_O$$

where $c_o$=hydrogen concentration in the specimen in mole-H/cm$^3$ and $c_A$=hydrogen concentration in the absorber in mole-H/cm$^3$.

For the experiment a case is realized, where the base areas of both materials are equal and the last equation is simplified to $$C_A = \frac{d_P}{d_A} C_O$$

where d is the thickness of the corresponding material. With the experimental value of $c_0$=1.8E-2 mole-H/cm$^3$ a value of $c_A$=3.6E-2 mole-H/cm$^3$ or 0.46 wt.-ppm, respectively is calculated in good agreement with the value obtained from the hot extraction determination.

As a rule for the important cases of application of the present invention the volume of the specimen $V_P$ is large or very large in comparison with the volume of the absorber $V_A$. These are the cases where a given component is the specimen which dimensions cannot be changed of course. In these cases a measure of the total concentration and the mobility of hydrogen can be obtained from the measured hydrogen concentration of the absorber $c_A$. This can be done as follows.

Before contacting the material of the specimen (first material) with the absorber (second material) or before transferring the hydrogen from the sample into the absorber (if sample material and absorber are contacted already), respectively the hydrogen concentration is equal to $c_0$ everywhere within the specimen. An (ideally chosen) absorber reduced then the hydrogen concentration in the specimen at the contact area between specimen and absorber to the value of zero. For this boundary condition the hydrogen amount per contact area $M_t$ transferred to the absorber is calculated as a function of time by $$M_t = c_0 \sqrt{\frac{Dt}{\pi}}.$$

Thereby D is the diffusion coefficient of hydrogen in the material of the specimen (first material). This diffusion coefficient is either already known from literature or may be determined experimentally for the related sample material by known techniques. $M_t$ is the amount of hydrogen being accumulated within the absorber. $M_t$ can be determined experimentally by various techniques as well (see corresponding explanations in the description). With the aid of these values the last equation yields the hydrogen concentration $c_0$ within the sample material. However, the last equation is valid only as long as at the most distant points from the absorber/sample contact area the initial hydrogen concentration $c_0$ was not lowered yet. In the present example this will be the case for times less 0.4 $d_p^2$/D =4000 s.

$M_t$ is not only important for the determination of the concentration $c_0$ but is furthermore an interesting value for the decision, whether a sample material contains a hydrogen concentration, which leads or could lead to hydrogen embrittlement. Hence the measurement or determination of the quantity $M_t$ could be of an even higher value than the determination of $c_0$, as for instance the enrichment of hydrogen at a newly formed crack is determined by the product $c_0\sqrt{D}$, too. Therefore, $M_t$ or the product $c_0\sqrt{D}$ evaluated from it respectively is a measure of the propensity of the sample material to hydrogen embrittlement.

If this consideration is transferred to the example given before with the values of D and $c_0$ mentioned there, then the last equation yields for $M_t$ $$M_t = 2.2 \cdot 10^{-9} \left[ \frac{\text{mole-H}}{\text{cm}^2 \sqrt{s}} \right] \sqrt{t}.$$

The amount of hydrogen transferred into the absorber causes a change of the hydrogen concentration in the absorber $\Delta c$ which depends on the volume $V_A$ of the absorber. If a layer of absorber material of thickness d is used as in the present example, then the following relation is obtained with d measured in cm $$\Delta c = 2.2 \cdot 10^{-9} \left[ \frac{\text{mole-H}}{\text{cm}^2 \sqrt{s}} \right] \frac{\sqrt{t}}{d}.$$

With the molar volume $V_a$ (in cm$^3$/mole) of the absorber the change of hydrogen concentration in the absorber in at.-% is given as $$\Delta c = \frac{2.2 \cdot 10^{-7} V_a \sqrt{t}}{d} at.-\%.$$

For the niobium layer mentioned in the example the last equation yields for $\Delta c$ a value of 3.6 at.-% using the corresponding values for $V_a$ and d as well as t=900 s. This corresponds in good agreement to the value of $\Delta c$=2.4 at.-% experimentally determined (by an electrochemical technique) in the example as the change of hydrogen concentration in the niobium layer. This agreement between experimental value and the one derived from the given equations demonstrates that the assumed diffusion coefficient of 1E−6 cm$^2$/s is reasonable.

Then in practice the following procedure is used. The hydrogen concentration or the change of the concentration of hydrogen (gaseous impurity), respectively within the absorber (second material, e.g. niobium) is determined quantitatively for instance by an electrochemical technique or by X-ray diffraction. With the aid of given equations and the known parameters (diffusion coefficient D of hydrogen within the specimen, thickness d of the absorber layer and molar volume $V_a$) the (initial) hydrogen concentration $c_0$ within the specimen is evaluated. In addition, the quantity $M_t$ can be evaluated this way.

Within the invention it is understood that especially the diffusion time (measuring time, time of the experiment) as well as the thickness d of the absorber layer can be varied within wide limits and correspondingly can be fitted to the respective sample material and its dimensions/volumes. Thus as a rule it will be such that for lower hydrogen contents in the specimen thinner absorber layers lead to a more precise result whereas for instance for larger hydrogen contents in the specimen thicker absorber layers are reasonable. For the measuring technique described in the example the niobium layer for instance can be reduced down to a thickness of 20 nm.

As already explained in the description the example can be modified such that on the same steel sample different (second) materials with different thermodynamic affinities to hydrogen can be deposited as absorbers. This allows statements about how strongly the hydrogen within the sample is bound.

In the previous discussion an (ideally chosen) absorber was assumed, which has a very high affinity to hydrogen and, therefore, absorbs the total amount of hydrogen contained in the specimen. Such an (ideally chosen) absorber reduced the hydrogen concentration at the contact area (interface between specimen and absorber) to a value of zero (cf. equation before). A less strong absorber with lower affinity to hydrogen (absorber i) may for instance reduce for instance the hydrogen concentration to a value of $c_i$ only. Then the corresponding equation given before is modified to $$M_t = (c_0 - c_i)\sqrt{\frac{Dt}{\pi}}.$$

Then the hydrogen amount absorbed by the i-th absorber is reduced accordingly. A comparison with the (ideal) absorber yields the value $c_i$, which is a measure of the binding strength of the fraction of hydrogen ($c_0$-$c_i$) remaining in the sample.

EXAMPLE 2

A borehole with a diameter of 0.9 mm and a depth of 1 mm was set in the middle of the end plane of two steel cylinders (of the types ST37 and 9S20K) having a diameter of 10 mm and a height of 3 mm. Into the borehole a sharpened vanadium wire with a diameter of 1 mm was pressed (friction welded) by the aid of a drilling machine. On the adjacent end plane of the steel cylinders hydrogen was generated by anodic polarization using an electrolyte of 1 N sulphuric acid saturated with arsenic trioxide and applying a current density of 50 to 100 mA/cm$^2$. A constant increase of the resistivity of the adjacent vanadium wire was detected after a time lag of one hour for the ST37 steel or several hours for the 9S20K-steel, respectively. The change was up to 1E−3 per hour, which corresponds to a concentration change of 0.02 at.-% within the vanadium wire. Using these values the hydrogen concentration of the steel at the side in contact with the electrolyte is calculated to be 2 wt.-ppm. A more precise calculation of this concentration for the exact existing boundary conditions becomes possible by a numerical solution of Fick's Second Law. During the measurement of the electrical resistivity of the vanadium wire a current of 100 mA was passed through the wire and an additional vanadium wire in series which was not in contact with the corresponding steel and, therefore, was not able to absorb hydrogen from the steel samples. The voltage drop over a distance of 8 mm was measured several times during a second for both wires. From the averaged difference of the voltage drops in both wires which was divided by the averaged voltage drop of the additional wire resistivity changes less than 1E−3 could be measured for the wire contacted to the steel samples.

The invention claimed is:

1. A method for detecting hydrogen comprising:
   providing a first sample of a first material, said first material comprising steel and including a first concentration of hydrogen;
   transferring a portion of said hydrogen from said first sample of said first material to a second material, said second material comprising niobium, palladium, tantalum, or vanadium, said transferred hydrogen having a second concentration in said second material; and
   detecting the presence of said transferred hydrogen in said second material.

2. The method of claim 1, wherein said detecting of said hydrogen in said second material includes an X-ray diffraction measurement.

3. The method of claim 1, wherein said detecting of said hydrogen in said second material includes an electrochemical measurement.

4. The method of claim 1, wherein said detecting of said hydrogen in said second material includes a measurement of electrical resistivity.

5. The method of claim 1, wherein said detecting of said hydrogen includes measuring the amount per unit area of said hydrogen absorbed by said second material as a function of time.

6. The method of claim 1, further comprising:
   providing a second sample of said first material; and
   transferring a second portion of said hydrogen from said second sample of said first material to a third material.

7. The method of claim 6, further comprising detecting the presence of said hydrogen in said third material.

8. The method of claim 7, further comprising calculating the binding strength of said hydrogen in said first material, said calculating combining a result from said detecting the presence of said hydrogen in said second material and a result from said detecting said hydrogen in said third material.

9. The method of claim 1, wherein said transferring includes contacting said second material with said first sample of said first material.

10. The method of claim 9, wherein said portion of said hydrogen is transferred from said first sample of said first material into said second material by diffusion.

11. The method of claim 9, wherein said transfer of said portion of said hydrogen from said first sample of said first material into said second material is achieved by applying an electric field.

12. The method of claim 9, wherein said second material is contacted in an elongated form with said first sample of said first material.

13. The method of claim 12, wherein said elongated form is a ribbon, bolt or wire.

14. The method of claim 9, wherein said second material is contacted with said first sample of said first material by welding.

15. The method of claim 14, wherein said welding is friction welding.

16. The method of claim 14, wherein said welding is thermal welding.

17. The method of claim 9, wherein said contacting comprises depositing said second material as a layer on said first sample of said first material.

18. The method of claim 17, wherein said layer of said second material is less than 1 µm thick.

19. The method of claim 18, wherein said layer of the said second material is less than 250 nm thick.

20. The method of claim 19, wherein said layer of said second material is in between 10 and 100 nm thick.

21. The method of claim 17, wherein said layer of said second material is deposited by a CVD technique.

22. The method of claim 17, wherein said layer of said second material is deposited by a PVD technique.

23. The method of claim 1, wherein said detecting includes measuring said second concentration.

24. The method of claim 1, wherein said transfer occurs until the concentration of said hydrogen in said second material is higher than the initial concentration of said hydrogen in said first sample of said first material.

25. The method of claim 1, further comprising calculating said first concentration, said calculating utilizing a result obtained from said detecting said hydrogen in said second material.

26. The method of claim 1, wherein said first sample of said first material is incorporated in an object, said object including a third material.

27. The method of claim 1, wherein said second material has an elongated shape.

* * * * *